(12) United States Patent
LeVan, Jr. et al.

(10) Patent No.: US 10,099,072 B2
(45) Date of Patent: Oct. 16, 2018

(54) ADSORBENT MATERIALS AND METHODS OF MAKING AND USE THEREOF

(71) Applicant: Vanderbilt University, Nashville, TN (US)

(72) Inventors: Martin Douglas LeVan, Jr., The Villages, FL (US); Dushyant Barpaga, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 63 days.

(21) Appl. No.: 15/378,128

(22) Filed: Dec. 14, 2016

(65) Prior Publication Data
US 2017/0296849 A1 Oct. 19, 2017

Related U.S. Application Data

(60) Provisional application No. 62/267,420, filed on Dec. 15, 2015.

(51) Int. Cl.
| | |
|---|---|
| *B01J 20/10* | (2006.01) |
| *A62B 23/02* | (2006.01) |
| *A61L 31/14* | (2006.01) |
| *A61L 31/02* | (2006.01) |
| *A61L 31/08* | (2006.01) |
| *A61M 16/10* | (2006.01) |
| *A41D 13/00* | (2006.01) |

(52) U.S. Cl.
CPC ........ *A62B 23/025* (2013.01); *A41D 13/0002* (2013.01); *A61L 31/022* (2013.01); *A61L 31/08* (2013.01); *A61L 31/146* (2013.01); *A61M 16/105* (2013.01); *B01J 20/10* (2013.01); *A41D 2400/22* (2013.01); *A61M 2205/7536* (2013.01)

(58) Field of Classification Search
CPC ...................................................... B01J 20/10
See application file for complete search history.

(56) References Cited

U.S. PATENT DOCUMENTS

| | | | |
|---|---|---|---|
| 3,974,318 A | 8/1976 | Lilla | |
| 5,063,196 A | 11/1991 | Doughty et al. | |
| 5,196,380 A * | 3/1993 | Shadman | B01D 53/22 210/500.25 |
| 5,492,882 A | 2/1996 | Doughty et al. | |
| 5,637,544 A * | 6/1997 | Shadman | B01D 53/22 427/245 |
| 5,705,221 A | 1/1998 | Yoerger et al. | |
| 5,897,673 A | 4/1999 | Nishida et al. | |
| 6,733,828 B2 | 5/2004 | Chao et al. | |
| 2008/0236389 A1 | 10/2008 | Leedy et al. | |
| 2012/0088033 A1 | 4/2012 | Sheeby | |
| 2013/0316898 A1 | 11/2013 | De Leij et al. | |

OTHER PUBLICATIONS

Arcibar-Orozcoa, et al., "Reactive adsorption of $SO_2$ on activated carbons with deposited iron nanoparticles." J. Hazard. Mater 246-247, 2013, 300-309.
Barpaga, et al., "Functionalization of carbon silica composites with active metal sites for $NH_3$ and $SO_2$ adsorption." Microporous Mesoporous Mater. 221, 2016, 197-203.
Bashkova, et al., "Effect of surface chemical and structural heterogeneity of copper-based MOF/graphite oxide composites on the adsorption of ammonia", J. Colloid Interface Sci. 417, 2014, 109-114.
Fortier, et al., "Ammonia, cyclohexane, nitrogen and water adsorption capacities of an activated carbon impregnated with increasing amounts of $ZnCl_2$, and designed to chemisorb gaseous $NH_3$ from an air stream.", J. Colloid Interface Sci. 320, 2008, 423-435.
Fortier, et al., "$SO_2$ adsorption capacity of $K_2CO_3$-impregnated activated carbon as a function of $K_2CO_3$ content loaded by soaking and incipient wetness", Appl. Surf. Sci., 2007, 3201-3207.
Froba, et al., "Iron (III) oxide nanoparticles within the pore system of mesoporous carbon CMK-1: intra-pore synthesis and characterization, "Microporous Mesoporous Mater. 60, 2003, 151-158.
Froba, et al., "Synthesis and characterization of Au55 clusters within mesoporous silica", Z. Anorg. Allg. Chem. 631, 2005, 2800-2805.
Furtado, et al., "Carbon silica composites for sulfur dioxide and ammonia adsorption", Microporous Mesoporous Mater. 165, 2013, 48-54.
Furtado, et al., "MCM-41 impregnated with active metal sites: synthesis, characterization and ammonia adsorption", Microporous Mesoporous Mater. 142, 2011, 730-739.
Furtado, et al., "Organoalkoxysilane-grafted silica composites for acidic and basic gas adsorption", Langmuir 28, 2012, 17450-17456.
Glover, et al., "Carbon—silica composite adsorbent: characterization and adsorption of light gases", Microporous Mesoporous Mater. 111, 2008, 1-11.
Glover, et al., "Carbon—silica composite adsorbent: sensitivity to synthesis conditions", Microporous Mesoporous Mater. 118, 2009, 21-27.
Kresge, et al., "Ordered mesoporous molecular sieves synthesized by a liquid crystal template mechanism", Nature 359, 1992, 710-712.

(Continued)

*Primary Examiner* — Stuart L Hendrickson
(74) *Attorney, Agent, or Firm* — Meunier Carlin & Curfman LLC (57) ABSTRACT

Disclosed are adsorbent materials that comprise a porous material having a continuous silica phase coated with a carbon layer, and a water-insoluble precipitate comprising a metal cation and an anion disposed substantially evenly throughout the adsorbent material. In some examples, the plurality of pores can have an average characteristic dimension of from 0.1 Å to 100 Å. The water-insoluble precipitate can be formed in the plurality of pores of the porous material by contacting the porous material with a first aqueous solution comprising a metal cation; and contacting the porous material with a second aqueous solution comprising an anion; wherein the metal cation and the anion combine to form the water-insoluble precipitate in the plurality of pores of the porous material, thereby forming the adsorbent material.

19 Claims, 3 Drawing Sheets

(56) References Cited

OTHER PUBLICATIONS

Leleuch, et al., "The role of water and surface acidity on the reactive adsorption of ammonia on modified activated carbons.", Carbon 45, 2007, 568-578.

Romero, et al., "$SO_2$ and $NH_3$ gas adsorption on a ternary ZnO/CuO/$CuCl_2$ impregnated activated carbon evaluated using combinatorial methods", ACS Comb. Sci. 14, 2012, 31-37.

Smith, et al., "Investigation of copper oxide impregnants prepared from various precursors for respirator carbons", J. Colloid Interface Sci. 341, 2010, 162-170.

Smith, et al., "Understanding the role of each ingredient in a basic copper carbonate based impregnation recipe for respirator carbons", J. Colloid Interface Sci. 337, 2009, 313-321.

Borelli, ed. Bioterrorism: Prevention, Preparedness, and Protection. Nova Science Publishers, Inc. NY, 2007, pp. 36-97.

Deliyanni et al., Impregnation of activated carbon by iron oxyhydroxide and its effect on aresenate removal. Jounral of Chemical Technology and Biotechnology, 2013, 88(6), 1058-1066.

Popa et al. Acidic and neutral caesium salts of 12-molybdophosphoric acid supported on SBA-15 mesoporous silica The influence of Cs concentration and surface coverage on textural and structural properties. Materials Research Bulletin, 2014, 50, 312-322.

Popa et al. The influence of surface coverage on textural, structural, and catalytic properties of cesium salts of 12-molybdophosphoric acid supported on SBA-15 mesoporous silica. Microporous and Mesoporous Materials, 2012, 156, 127-137.

Zhao et al., Preparation of $Cu_xCe(1-x)O(2-x)$/SBA-15 catalysts and the catalytic properties of CO oxidation. Journal of Porous Materials, 2012, 19(5), 869-876.

MSDS, ASZMTEDA, Calgo Carbon Corporation.

\* cited by examiner

ADSORBENT MATERIALS AND METHODS OF MAKING AND USE THEREOF

CROSS-REFERENCE TO RELATED APPLICATIONS

This application claims the benefit of U.S. Provisional Application No. 62/267,420, filed Dec. 15, 2015, which is hereby incorporated herein by reference in its entirety.

STATEMENT OF GOVERNMENT SUPPORT

This invention was made with government support under Grant No. W911SR-13-C-0014 awarded by the United States Army. The government has certain rights in this invention.

BACKGROUND

Activated carbon has long been used to remove toxic gases and vapors from a stream of gas or liquid. These activated carbons are also useful in cleaning breathing air or exhaust gases by removing various noxious agents, and may be used in gas mask filters, respirators, filters and other applications, and often involve the use of special impregnants to remove gases that would not otherwise be removed through the use of unimpregnated, activated carbons. In many applications, it is desirable that a single impregnated adsorbent be effective against a range of toxic agents in a gas stream. Thus what are needed are new adsorbents that have wider or more effective applications. The subject matter disclosed herein addresses these and other needs.

SUMMARY

Disclosed herein are adsorbent materials. The adsorbent materials can, for example, comprise a porous material comprising a continuous silica phase coated with a layer comprising carbon and permeated by a plurality of pores, wherein a water-insoluble precipitate comprising a metal cation and an anion is disposed substantially evenly throughout the adsorbent material within the plurality of pores. The continuous silica phase can, for example, comprise a mesoporous silica. In some examples, the continuous silica phase can comprise MCM-41. The carbon layer can, for example, comprise a carbonized alcohol. In some examples, the carbon layer can comprise carbonized furfuryl alcohol. The porous material can, in some examples, have a BET surface area of from 500 to 1000 m$^2$/g. In some examples, the porous material can have a pore volume of from 0.3 to 1.2 cm$^3$/g. In some examples, the plurality of pores can have an average characteristic dimension of from 0.1 Å to 100 Å (e.g., from 0.1 Å to 50 Å, from 0.1 Å to 10 Å).

In some examples, the water-insoluble precipitate can be formed in the plurality of pores of the porous material by contacting the porous material with a first aqueous solution comprising a metal cation; and contacting the porous material with a second aqueous solution comprising an anion; wherein the metal cation and the anion combine to form the water-insoluble precipitate in the plurality of pores of the porous material, thereby forming the adsorbent material.

In some examples, the porous material can be contacted with the first aqueous solution before being contacted with the second aqueous solution. In some examples, the porous material can be contacted with the second aqueous solution before being contacted with the first aqueous solution. In some examples, the porous material can be contacted with the first aqueous solution and the second aqueous solution simultaneously.

In some examples, the porous material can be contacted with the first aqueous solution for an amount of time from greater than 0 to 48 hours. In some examples, the porous material can be contacted with the second aqueous solution for an amount of time from greater than 0 to 48 hours.

The metal cation can comprise, for example, a single or multivalent metal cation. In some examples, the metal cation can comprise a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, Ra, La, Ce, Pr, Nd, Sm, Eu, Gd, Tb, Dy, Ho, Er, Tm, Yb, Lu, Th, Pa, U, Np, Pu, Am, Cm, Bk, and combinations thereof.

The anion can, for example, comprise chloride, bromide, iodide, fluoride, sulfate, sulfide, hydroxide, phosphate, carbonate, sulfite, oxide, silicate, chromate, or a combination thereof.

In some examples, the concentration of the water-insoluble precipitate in the adsorbent material can be from 10 wt. % to 20 wt. % of the adsorbent material.

In some examples, the water-insoluble precipitate can have a solubility of 0.1 g or less per 100 mL of water at 20° C.

In some examples, the water-insoluble precipitate can comprise magnesium phosphate, magnesium carbonate, zinc phosphate, copper carbonate, copper phosphate, zinc carbonate, or combinations thereof. In some examples, the water-insoluble precipitate comprises zinc carbonate.

In some examples, the adsorbent material can have a BET surface area of from 100 to 700 m$^2$/g. In some examples, the adsorbent material can have a pore volume of from 0.1 to 0.8 cm$^3$/g.

In some examples, the adsorbent material can have an adsorption capacity for NH$_3$ gas of from 0.3 to 6 mol of NH$_3$ per kg of adsorbent material (mol/kg). For example, the adsorbent material can have an adsorption capacity of 2 mol of NH$_3$ or more per kg of adsorbent material.

In some examples, the adsorbent material can have an adsorption capacity for SO$_2$ gas of from 0.05 to 0.7 mol of SO$_2$ per kg of adsorbent material (mol/kg). For example, the adsorbent material can have an adsorption capacity of 0.3 mol of SO$_2$ or more per kg of adsorbent material or more.

Also disclosed herein are methods of forming adsorbent materials. The methods of forming adsorbent materials can, for example, comprise contacting a porous material with a first aqueous solution comprising a metal cation; and contacting the porous material with a second aqueous solution comprising an anion; wherein the metal cation and the anion combine to form a water-insoluble precipitate in the plurality of pores of the porous material, thereby forming the adsorbent material. In some examples, the method can further comprise washing the adsorbent material to substantially remove a residual water-soluble ion.

Also disclosed herein are filters for removing a gas from a gas stream, said filter comprising any of the adsorbent materials described herein. Also disclosed herein are respirators comprising any of the filters disclosed herein. Also disclosed herein are gas masks comprising any of the filters described herein. The adsorbent materials, filters, respirators, and/or gas masks described herein can, for example, be used for military, homeland security, first responder, civilian, and/or industrial applications.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

The compositions and methods described herein may be understood more readily by reference to the following detailed description of specific aspects of the disclosed subject matter and the Examples and Figures included therein.

Before the present compositions and methods are disclosed and described, it is to be understood that this disclosure is not limited to specific synthetic methods or to particular reagents, as such may, of course, vary. It is also to be understood that the terminology used herein is for the purpose of describing particular embodiments only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

"Phase," as used herein, generally refers to a region of a material having a substantially uniform composition which is a distinct and physically separate portion of a heterogeneous system. The term "phase" does not imply that the substance(s) making up a phase is a chemically pure substance, but merely that the chemical and/or physical properties of the substance making up the phase are essentially uniform throughout the material, and that these chemical and/or physical properties differ significantly from the chemical and/or physical properties of another phase within the material. Examples of physical properties include density, thickness, aspect ratio, specific surface area, porosity and dimensionality. Examples of chemical properties include chemical composition.

"Continuous," as used herein, generally refers to a phase such that all points within the phase are directly connected, so that for any two points within a continuous phase, there exists a path which connects the two points without leaving the phase.

The term "characteristic dimension," as used herein, refers to the largest cross-sectional dimension of a pore in a plane perpendicular to the longitudinal axis of the pore. For example, in the case of a substantially cylindrical pore in the porous material, the characteristic dimension of the pore would be the diameter of the pore.

The characteristic dimension of a pore can be determined, for example, using electron microscopy (e.g., scanning electron microscopy (SEM), transmission electron microscopy (TEM), high-resolution TEM (HRTEM), scanning transmission electron microscopy (STEM)), Brunauer-Emmett-Teller (BET) measurements, or a combination thereof. As used herein, the characteristic pore dimension is determined using Brunauer-Emmett-Teller (BET) measurements.

The term "precipitate" refers to a solid phase that is separated from a solution.

The term "comprising" and variations thereof as used herein is used synonymously with the term "including" and variations thereof and are open, non-limiting terms. Although the terms "comprising" and "including" have been used herein to describe various examples, the terms "consisting essentially of" and "consisting of" can be used in place of "comprising" and "including" to provide for more specific examples of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

It is understood that throughout this specification the identifiers "first", "second" and "third" are used solely to aid in distinguishing the various components and steps of the disclosed subject matter. The identifiers "first", "second" and "third" are not intended to imply any particular order, amount, preference, or importance to the components or steps modified by these terms.

As used herein, "water-insoluble precipitate" means that the material has a solubility of 1 g or less per 1000 mL of water at 20° C.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Reference will now be made in detail to specific aspects of the disclosed materials, compounds, compositions, articles, and methods, examples of which are illustrated in the accompanying examples and figures.

Adsorbent Materials

Disclosed herein are adsorbent materials. The adsorbent materials can, for example, comprise a porous material comprising a continuous silica phase coated with a layer comprising carbon and permeated by a plurality of pores, wherein a water-insoluble precipitate comprising a metal cation and an anion is disposed substantially evenly throughout the adsorbent material within the plurality of pores. In some examples, the adsorbent materials can comprise a substrate material comprising a continuous silica phase coated with a layer comprising carbon, wherein the substrate material is non-porous and wherein a water-insoluble precipitate comprising a metal cation and an anion is disposed substantially evenly throughout and/or around the adsorbent material.

The continuous silica phase can, for example, comprise a mesoporous silica. Examples of mesoporous silica include, for example, MCM- (e.g., MCM-41, MCM-48), SBA-15, MSU-, KSW-, FSM-, HMM-, and combinations thereof. In some examples, the continuous silica phase can comprise MCM-41.

The carbon layer can, for example, comprise a carbon compound, such as an alcohol, carboxylic acid (e.g., acetylenedicarboxylic acid), sugar (e.g., sucrose), polymer (e.g., polyacrylonitrile, polyvinyl alcohol), derivatives thereof, or combinations thereof. In some examples, the carbon layer can comprise a carbonized compound, such as a carbonized alcohol, carbonized carboxylic acid (e.g., acetylenedicarboxylic acid), carbonized sugar (e.g., sucrose), carbonized polymer (e.g., polyacrylonitrile, polyvinyl alcohol), derivatives thereof, or combinations thereof. In some examples, the carbon layer can comprise carbonized furfuryl alcohol.

The carbon layer can, for example, have an average thickness of 0.1 Å or more (e.g., 0.2 Å or more, 0.3 Å or more, 0.4 Å or more, 0.5 Å or more, 0.6 Å or more, 0.7 Å or more, 0.8 Å or more, 0.9 Å or more, 1 Å or more, 1.5 Å or more, 2 Å or more, 2.5 Å or more, 3 Å or more, 3.5 Å or more, 4 Å or more, 4.5 Å or more, 5 Å or more, 5.5 Å or more, 6 Å or more, 6.5 Å or more, 7 Å or more, 7.5 Å or more, 8 Å or more, 8.5 Å or more, 9 Å or more, 9.5 Å or more, 10 Å or more, 11 Å or more, 12 Å or more, 13 Å or more, 14 Å or more, 15 Å or more, 16 Å or more, 17 Å or more, 18 Å or more, 19 Å or more, 20 Å or more, 25 Å or more, 30 Å or more, 35 Å or more, 40 Å or more, 45 Å or more, 50 Å or more, 55 Å or more, 60 Å or more, 65 Å or more, 70 Å or more, 75 Å or more, 80 Å or more, 85 Å or more, 90 Å or more, or 95 Å or more). In some examples, the carbon layer can have an average thickness of 100 Å or less (e.g., 95 Å or less, 90 Å or less, 85 Å or less, 80 Å or less, 75 Å or less, 70 Å or less, 65 Å or less, 60 Å or less, 55 Å or less, 50 Å or less, 45 Å or less, 40 Å or less, 35 Å or less, 30 Å or less, 25 Å or less, 20 Å or less, 19 Å or less, 18 Å or less, 17 Å or less, 16 Å or less, 15 Å or less, 14 Å or less, 13 Å or less, 12 Å or less, 11 Å or less, 10 Å or less, 9.5 Å or less, 9 Å or less, 8.5 Å or less, 8 Å or less, 7.5 Å or less, 7 Å or less, 6.5 Å or less, 6 Å or less, 5.5 Å or less, 5 Å or less, 4.5 Å or less, 4 Å or less, 3.5 Å or less, 3 Å or less, 2.5 Å or less, 2 Å or less, 1.5 Å or less, 1 Å or less, 0.9 Å or less, 0.8 Å or less, 0.7 Å or less, 0.6 Å or less, 0.5 Å or less, 0.4 Å or less, 0.3 Å or less, or 0.2 Å or less).

The average thickness of the carbon layer can range from any of the minimum values described above to any of the maximum values described above. For example, the carbon layer can have an average thickness of from 0.1 Å to 100 Å (e.g., from 0.1 Å to 50 Å, from 50 Å to 100 Å, from 0.1 Å to 20 Å, from 20 Å to 40 Å, from 40 Å to 60 Å, from 60 Å to 80 Å, from 80 Å to 100 Å, from 1 Å to 90 Å, or from 0.1 Å to 10 Å).

The surface area of the porous material can be determined, for example, using Brunauer-Emmett-Teller (BET) theory. The porous material can, in some examples, have a BET surface area of 500 $m^2/g$ or more (e.g., 505 $m^2/g$ or more, 510 $m^2/g$ or more, 515 $m^2/g$ or more, 520 $m^2/g$ or more, 525 $m^2/g$ or more, 530 $m^2/g$ or more, 535 $m^2/g$ or more, 540 $m^2/g$ or more, 545 $m^2/g$ or more, 550 $m^2/g$ or more, 555 $m^2/g$ or more, 560 $m^2/g$ or more, 565 $m^2/g$ or more, 570 $m^2/g$ or more, 575 $m^2/g$ or more, 580 $m^2/g$ or more, 585 $m^2/g$ or more, 590 $m^2/g$ or more, 595 $m^2/g$ or more, 600 $m^2/g$ or more, 625 $m^2/g$ or more, 650 $m^2/g$ or more, 675 $m^2/g$ or more, 700 $m^2/g$ or more, 725 $m^2/g$ or more, 750 $m^2/g$ or more, 775 $m^2/g$ or more, 800 $m^2/g$ or more, 825 $m^2/g$ or more, 850 $m^2/g$ or more, 875 $m^2/g$ or more, 900 $m^2/g$ or more, 925 $m^2/g$ or more, 950 $m^2/g$ or more, or 975 $m^2/g$ or more).

In some examples, the porous material can have a BET surface area of 1000 $m^2/g$ or less (e.g., 975 $m^2/g$ or less, 950 $m^2/g$ or less, 925 $m^2/g$ or less, 900 $m^2/g$ or less, 875 $m^2/g$ or less, 850 $m^2/g$ or less, 825 $m^2/g$ or less, 800 $m^2/g$ or less, 775 $m^2/g$ or less, 750 $m^2/g$ or less, 725 $m^2/g$ or less, 700 $m^2/g$ or less, 675 $m^2/g$ or less, 650 $m^2/g$ or less, 625 $m^2/g$ or less, 600 $m^2/g$ or less, 595 $m^2/g$ or less, 590 $m^2/g$ or less, 585 $m^2/g$ or less, 580 $m^2/g$ or less, 575 $m^2/g$ or less, 570 $m^2/g$ or less, 565 $m^2/g$ or less, 560 $m^2/g$ or less, 555 $m^2/g$ or less, 550 $m^2/g$ or less, 545 $m^2/g$ or less, 540 $m^2/g$ or less, 535 $m^2/g$ or less, 530 $m^2/g$ or less, 525 $m^2/g$ or less, 520 $m^2/g$ or less, 515 $m^2/g$ or less, 510 $m^2/g$ or less, or 505 $m^2/g$ or less).

The BET surface area of the porous material can range from any of the minimum values described above to any of the maximum values described above. For example, the porous material can have a BET surface area of from 500 to 1000 $m^2/g$ (e.g., from 500 $m^2/g$ to 750 $m^2/g$, from 750 $m^2/g$ to 1000 $m^2/g$, from 500 $m^2/g$ to 600 $m^2/g$, from 600 $m^2/g$ to 700 $m^2/g$, from 700 $m^2/g$ to 800 $m^2/g$, from 800 $m^2/g$ to 900 $m^2/g$, from 900 $m^2/g$ to 1000 $m^2/g$, or from 505 $m^2/g$ to 595 $m^2/g$).

Porosimetry (e.g., mercury porosimetry) and/or equilibrium nitrogen adsorption isotherms can, for example, be used to determine various aspects of the porous nature of the porous material, such as the average characteristic dimension of the plurality of pores, the total volume of the plurality of pores, the surface area of the porous material, the bulk density of the porous material, the absolute density of the porous material, or combinations thereof.

In some examples, the porous material can have a pore volume of 0.3 $cm^3/g$ or more (e.g., 0.325 $cm^3/g$ or more, 0.35 $cm^3/g$ or more, 0.375 $cm^3/g$ or more, 0.40 $cm^3/g$ or more, 0.425 $cm^3/g$ or more, 0.45 $cm^3/g$ or more, 0.475 $cm^3/g$ or more, 0.5 $cm^3/g$ or more, 0.55 $cm^3/g$ or more, 0.6 $cm^3/g$ or more, 0.65 $cm^3/g$ or more, 0.7 $cm^3/g$ or more, 0.75 $cm^3/g$ or more, 0.8 $cm^3/g$ or more, 0.85 $cm^3/g$ or more, 0.9 $cm^3/g$ or more, 0.95 $cm^3/g$ or more, 1.0 $cm^3/g$ or more, 1.05 $cm^3/g$ or more, 1.1 $cm^3/g$ or more, or 1.15 $cm^3/g$ or more). In some examples, the porous material can have a pore volume of 1.2 $cm^3/g$ or less (e.g., 1.15 $cm^3/g$ or less, 1.1 $cm^3/g$ or less, 1.05 $cm^3/g$ or less, 1.0 $cm^3/g$ or less, 0.95 $cm^3/g$ or less, 0.9 $cm^3/g$ or less, 0.85 $cm^3/g$ or less, 0.8 $cm^3/g$ or less, 0.75 $cm^3/g$ or less, 0.7 $cm^3/g$ or less, 0.65 $cm^3/g$ or less, 0.6 $cm^3/g$ or less, 0.55 $cm^3/g$ or less, 0.5 $cm^3/g$ or less, 0.475 $cm^3/g$ or less, 0.45 cm$^3$/g or less, 0.425 cm$^3$/g or less, 0.4 cm$^3$/g or less, 0.375 cm$^3$/g or less, 0.35 cm$^3$/g or less, or 0.325 cm$^3$/g or less).

The pore volume of the porous material can range from any of the minimum values described above to any of the maximum values described above. For example, the porous material can have a pore volume of from 0.3 to 1.2 cm$^3$/g (e.g., from 0.3 cm$^3$/g to 0.75 cm$^3$/g, from 0.75 cm$^3$/g to 1.2 cm$^3$/g, from 0.3 cm$^3$/g to 0.5 cm$^3$/g, from 0.5 cm$^3$/g to 0.7 cm$^3$/g, from 0.7 cm$^3$/g to 0.9 cm$^3$/g, from 0.9 cm$^3$/g to 1.2 cm$^3$/g, or from 0.325 cm$^3$/g to 0.675 cm$^3$/g).

In some examples, the plurality of pores can have an average characteristic dimension of 0.1 Å or more (e.g., 0.2 Å or more, 0.3 Å or more, 0.4 Å or more, 0.5 Å or more, 0.6 Å or more, 0.7 Å or more, 0.8 Å or more, 0.9 Å or more, 1 Å or more, 1.5 Å or more, 2 Å or more, 2.5 Å or more, 3 Å or more, 3.5 Å or more, 4 Å or more, 4.5 Å or more, 5 Å or more, 5.5 Å or more, 6 Å or more, 6.5 Å or more, 7 Å or more, 7.5 Å or more, 8 Å or more, 8.5 Å or more, 9 Å or more, 9.5 Å or more, 10 Å or more, 11 Å or more, 12 Å or more, 13 Å or more, 14 Å or more, 15 Å or more, 16 Å or more, 17 Å or more, 18 Å or more, 19 Å or more, 20 Å or more, 25 Å or more, 30 Å or more, 35 Å or more, 40 Å or more, 45 Å or more, 50 Å or more, 55 Å or more, 60 Å or more, 65 Å or more, 70 Å or more, 75 Å or more, 80 Å or more, 85 Å or more, 90 Å or more, or 95 Å or more). In some examples, the plurality of pores can have an average characteristic dimension of 100 Å or less (e.g., 95 Å or less, 90 Å or less, 85 Å or less, 80 Å or less, 75 Å or less, 70 Å or less, 65 Å or less, 60 Å or less, 55 Å or less, 50 Å or less, 45 Å or less, 40 Å or less, 35 Å or less, 30 Å or less, 25 Å or less, 20 Å or less, 19 Å or less, 18 Å or less, 17 Å or less, 16 Å or less, 15 Å or less, 14 Å or less, 13 Å or less, 12 Å or less, 11 Å or less, 10 Å or less, 9.5 Å or less, 9 Å or less, 8.5 Å or less, 8 Å or less, 7.5 Å or less, 7 Å or less, 6.5 Å or less, 6 Å or less, 5.5 Å or less, 5 Å or less, 4.5 Å or less, 4 Å or less, 3.5 Å or less, 3 Å or less, 2.5 Å or less, 2 Å or less, 1.5 Å or less, 1 Å or less, 0.9 Å or less, 0.8 Å or less, 0.7 Å or less, 0.6 Å or less, 0.5 Å or less, 0.4 Å or less, 0.3 Å or less, or 0.2 Å or less).

The average characteristic dimension of the plurality of pores can range from any of the minimum values described above to any of the maximum values described above. For example, the plurality of pores can have an average characteristic dimension of from 0.1 Å to 100 Å (e.g., from 0.1 Å to 50 Å, from 50 Å to 100 Å, from 0.1 Å to 20 Å, from 20 Å to 40 Å, from 40 Å to 60 Å, from 60 Å to 80 Å, from 80 Å to 100 Å, from 1 Å to 90 Å, or from 0.1 Å to 10 Å).

In some examples, the water-insoluble precipitate can be formed in the plurality of pores of the porous material by contacting the porous material with a first aqueous solution comprising a metal cation; and contacting the porous material with a second aqueous solution comprising an anion; wherein the metal cation and the anion combine to form the water-insoluble precipitate in the plurality of pores of the porous material, thereby forming the adsorbent material.

As used herein, contacting a porous material with a solution can comprise, for example, immersing the porous material in the solution, spraying the solution onto the porous material, or otherwise physically contacting the porous material with the solution. Examples of methods of physically contacting the porous material with the solution can include the incipient wetness method. In the incipient wetness method, a solution is added to a porous material, wherein the volume of solution added is about the same as the pore volume of the porous material. In the incipient wetness method, capillary action draws the solution into the pores. Solution added in excess of the porous material pore volume can cause the solution transport to change from a capillary action process to a diffusion process, which can be slower.

In some examples, the porous material can be contacted with the first aqueous solution before being contacted with the second aqueous solution. In some examples, the porous material can be contacted with the second aqueous solution before being contacted with the first aqueous solution. In some examples, the porous material can be contacted with the first aqueous solution and the second aqueous solution simultaneously.

In some examples, the porous material can be contacted with the first aqueous solution for an amount of time of greater than 0 hours (e.g., 0.25 hours or more, 0.5 hours or more, 0.75 hours or more, 1 hour or more, 2 hours or more, 3 hours or more, 4 hours or more, 5 hours or more, 6 hours or more, 7 hours or more, 8 hours or more, 9 hours or more, 10 hours or more, 11 hours or more, 12 hours or more, 13 hours or more, 14 hours or more, 15 hours or more, 16 hours or more, 17 hours or more, 18 hours or more, 19 hours or more, 20 hours or more, 21 hours or more, 22 hours or more, 23 hours or more, 24 hours or more, 25 hours or more, 26 hours or more, 27 hours or more, 28 hours or more, 29 hours or more, 30 hours or more, 31 hours or more, 32 hours or more, 33 hours or more, 34 hours or more, 35 hours or more, 36 hours or more, 37 hours or more, 38 hours or more, 39 hours or more, 40 hours or more, 41 hours or more, 42 hours or more, 43 hours or more, 44 hours or more, 45 hours or more, 46 hours or more, or 47 hours or more).

In some examples, the porous material can be contacted with the first aqueous solution for 48 hours or less (e.g., 47 hours or less, 46 hours or less, 45 hours or less, 44 hours or less, 43 hours or less, 42 hours or less, 41 hours or less, 40 hours or less, 39 hours or less, 38 hours or less, 37 hours or less, 36 hours or less, 35 hours or less, 34 hours or less, 33 hours or less, 32 hours or less, 31 hours or less, 30 hours or less, 29 hours or less, 28 hours or less, 27 hours or less, 26 hours or less, 25 hours or less, 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, 9 hours or less, 8 hours or less, 7 hours or less, 6 hours or less, 5 hours or less, 4 hours or less, 3 hours or less, 2 hours or less, or 1 hour or less).

The amount of time for which the porous material is contacted with the first aqueous solution can range from any of the minimum values described above to any of the maximum values described above. For example, the porous material can be contacted with the first aqueous solution for from greater than 0 hours to 48 hours (e.g., from greater than 0 hours to 24 hours, from 24 hours to 48 hours, from greater than 0 hours to 12 hours, from 12 hours to 24 hours, from 24 hours to 36 hours, from 36 hours to 48 hours, or from 12 hours to 48 hours).

In some examples, the porous material can be contacted with the second aqueous solution for an amount of time of greater than 0 hours (e.g., 0.25 hours or more, 0.5 hours or more, 0.75 hours or more, 1 hour or more, 2 hours or more, 3 hours or more, 4 hours or more, 5 hours or more, 6 hours or more, 7 hours or more, 8 hours or more, 9 hours or more, 10 hours or more, 11 hours or more, 12 hours or more, 13 hours or more, 14 hours or more, 15 hours or more, 16 hours or more, 17 hours or more, 18 hours or more, 19 hours or more, 20 hours or more, 21 hours or more, 22 hours or more, 23 hours or more, 24 hours or more, 25 hours or more, 26 hours or more, 27 hours or more, 28 hours or more, 29 hours or more, 30 hours or more, 31 hours or more, 32 hours or more, 33 hours or more, 34 hours or more, 35 hours or more, 36 hours or more, 37 hours or more, 38 hours or more, 39 hours or more, 40 hours or more, 41 hours or more, 42 hours or more, 43 hours or more, 44 hours or more, 45 hours or more, 46 hours or more, or 47 hours or more).

In some examples, the porous material can be contacted with the second aqueous solution for 48 hours or less (e.g., 47 hours or less, 46 hours or less, 45 hours or less, 44 hours or less, 43 hours or less, 42 hours or less, 41 hours or less, 40 hours or less, 39 hours or less, 38 hours or less, 37 hours or less, 36 hours or less, 35 hours or less, 34 hours or less, 33 hours or less, 32 hours or less, 31 hours or less, 30 hours or less, 29 hours or less, 28 hours or less, 27 hours or less, 26 hours or less, 25 hours or less, 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, 9 hours or less, 8 hours or less, 7 hours or less, 6 hours or less, 5 hours or less, 4 hours or less, 3 hours or less, 2 hours or less, or 1 hour or less).

The amount of time for which the porous material is contacted with the second aqueous solution can range from any of the minimum values described above to any of the maximum values described above. For example, the porous material can be contacted with the second aqueous solution for from greater than 0 hours to 48 hours (e.g., from greater than 0 hours to 24 hours, from 24 hours to 48 hours, from greater than 0 hours to 12 hours, from 12 hours to 24 hours, from 24 hours to 36 hours, from 36 hours to 48 hours, or from 12 hours to 48 hours).

The first aqueous solution and the second aqueous solution can be selected based on well-known solubility rules such that the metal cation and the anion combine to form the water-insoluble precipitate. In general, compounds that contain ions with different radii are soluble in water. Conversely, the least water-soluble salts are those of ions with similar radii. That is, in general, difference in size favors solubility in water. Empirically, an ionic compound MX tends to be soluble in water when the radius of $M^+$ (e.g., the metal cation) is smaller than that of $X^-$ (e.g., the anion) by about 80 picometers (pm).

The "General Solubility Rules" listed below are well known and easily available.

General Solubility rules:
1. All common compounds of Group I and ammonium ions are soluble.
2. All nitrates, acetates, and chlorates are soluble.
3. All binary compounds of the halogens (other than F) with metals are soluble, except
   those of Ag, Hg(I) and Pb. Pb halides are soluble in hot water.
4. All sulfates are soluble, except those of barium, strontium, calcium, lead, silver, and mercury (I). The latter three are slightly soluble.
5. Except for rule 1, carbonates, hydroxides, oxides, silicates, and phosphates are insoluble.
6. Sulfites are insoluble except for calcium, barium, strontium, magnesium, sodium, potassium, and ammonium.

Examples of water-soluble salts that can be used to form the first aqueous solution and/or the second aqueous solution include, but are not limited to, ammonium and alkali metal salts having chloride ($Cl^-$), bromide ($Br^-$), iodide ($I^-$), sulfate ($SO_4^{-2}$), sulfide ($S^{-2}$), hydroxide ($OH^-$), phosphate ($PO_4^{-3}$), carbonate ($CO_3^{-2}$), and sulfite ($SO_3^{-2}$) anions, various other water-soluble sulfates such as magnesium sulfate and copper sulfate, various other water-soluble sulfides such as magnesium sulfide, and various other water-soluble hydroxides such as barium hydroxide, strontium hydroxide, radium hydroxide, and thallium hydroxide.

The metal cation can comprise, for example, a single or multivalent metal cation. In some examples, the metal cation can comprise a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, Ra, La, Ce, Pr, Nd, Sm, Eu, Gd, Tb, Dy, Ho, Er, Tm, Yb, Lu, Th, Pa, U, Np, Pu, Am, Cm, Bk, and combinations thereof. By "combinations thereof" is meant either a chemical combination or physical combination.

The anion can, for example, comprise chloride, bromide, iodide, fluoride, sulfate, sulfide, hydroxide, phosphate, carbonate, sulfite, oxide, silicate, chromate, or a combination thereof.

In some examples, the concentration of the water-insoluble precipitate in the adsorbent material can be 10 wt. % or more of the adsorbent material (e.g., 10.5 wt. % or more, 11 wt. % or more, 11.5 wt. % or more, 12 wt. % or more, 12.5 wt. % or more, 13 wt. % or more, 13.5 wt. % or more, 14 wt. % or more, 14.5 wt. % or more, 15 wt. % or more, 15.5 wt. % or more, 16 wt. % or more, 16.5 wt. % or more, 17 wt. % or more, 17.5 wt. % or more, 18 wt. % or more, 18.5 wt. % or more, 19 wt. % or more, or 19.5 wt. % or more). In some examples, the concentration of the water-insoluble precipitate in the adsorbent material can be 20 wt. % or less of the adsorbent material (e.g., 19.5 wt. % or less, 19 wt. % or less, 18.5 wt. % or less, 18 wt. % or less, 17.5 wt. % or less, 17 wt. % or less, 16.5 wt. % or less, 16 wt. % or less, 15.5 wt. % or less, 15 wt. % or less, 14.5 wt. % or less, 14 wt. % or less, 13.5 wt. % or less, 13 wt. % or less, 12.5 wt. % or less, 12 wt. % or less, 11.5 wt. % or less, 11 wt. % or less, or 10.5 wt. % or less).

The concentration of the water-insoluble precipitate in the adsorbent material can range from any of the minimum values described above to any of the maximum values described above. For example, the concentration of the water-insoluble precipitate in the adsorbent material can be from 10 wt. % to 10 wt. % of the adsorbent material (e.g., from 10 wt. % to 15 wt. %, from 15 wt. % to 20 wt. %, from 10 wt. % to 12 wt. %, from 12 wt. % to 14 wt. %, from 14 wt. % to 16 wt. %, from 16 wt. % to 18 wt. %, from 18 wt. % to 20 wt. %, or from 12 wt. % to 18 wt. %).

In some examples, the water-insoluble precipitate can have a solubility of 0.1 g or less per 100 mL of water at 20° C. (e.g., $7.5 \times 10^{-2}$ g or less, $5 \times 10^{-2}$ g or less, $2.5 \times 10^{-2}$ g or less, $1 \times 10^{-2}$ g or less, $7.5 \times 10^{-3}$ g or less, $5 \times 10^{-3}$ g or less, $2.5 \times 10^{-3}$ g or less, $1 \times 10^{-3}$ g or less, $7.5 \times 10^{-4}$ g or less, $5 \times 10^{-4}$ g or less, $2.5 \times 10^{-4}$ g or less, $1 \times 10^{-4}$ g or less, $7.5 \times 10^{-5}$ g or less, $5 \times 10^{-5}$ g or less, $2.5 \times 10^{-5}$ g or less, $1 \times 10^{-5}$ g or less, $7.5 \times 10^{-6}$ g or less, $5 \times 10^{-6}$ g or less, $2.5 \times 10^{-6}$ g or less, $1 \times 10^{-6}$ g or less, $7.5 \times 10^{-7}$ g or less, $5 \times 10^{-7}$ g or less, $2.5 \times 10^{-7}$ g or less, $1 \times 10^{-7}$ g or less, $7.5 \times 10^{-8}$ g or less, $5 \times 10^{-8}$ g or less, $2.5 \times 10^{-8}$ g or less, $1 \times 10^{-8}$ g or less, $7.5 \times 10^{-9}$ g or less, $5 \times 10^{-9}$ g or less, $2.5 \times 10^{-9}$ g or less, $1 \times 10^{-9}$ g or less, $7.5 \times 10^{-10}$ g or less, $5 \times 10^{-10}$ g or less, $2.5 \times 10^{-10}$ g or less, $1 \times 10^{-10}$ g or less, $5 \times 10^{-11}$ g or less, $1 \times 10^{-11}$ g or less, $5 \times 10^{-12}$ g or less, $1 \times 10^{-12}$ g or less, $5 \times 10^{-13}$ g or less, $1 \times 10^{-13}$ g or less, $5 \times 10^{-14}$ g or less, $1 \times 10^{-14}$ g or less, $5 \times 10^{-15}$ g or less, $1 \times 10^{-15}$ g or less, $1 \times 10^{-16}$ g or less, $1 \times 10^{-17}$ g or less, $1 \times 10^{-18}$ g or less, $1 \times 10^{-19}$ g or less, $1 \times 10^{-20}$ g or less, $1\times10^{-21}$ g or less, $1\times10^{-22}$ g or less, $1\times10^{-23}$ g or less, $1\times10^{-24}$ g or less, or $1\times10^{-25}$ g or less).

Examples of water-insoluble precipitates include, for example, nickel hydroxide, silver chloride, silver bromide, silver iodide, lead chloride, lead bromide, lead iodide, mercury chloride, copper chloride, mercury bromide, copper bromide, mercury iodide, copper iodide, thallium chloride, thallium bromide, thallium iodide, silver sulfate, lead sulfate, barium sulfate, strontium sulfate, calcium sulfate, radium sulfate, zinc sulfide, silver hydroxide, magnesium carbonate, copper carbonate, cerium carbonate, barium carbonate, manganese carbonate, iron carbonate, cobalt carbonate, nickel carbonate, silver carbonate, zinc carbonate, cadmium carbonate, aluminum carbonate, tellurium carbonate, lead carbonate, lanthanum carbonate, magnesium phosphate, copper phosphate, cerium phosphate, barium phosphate, manganese phosphate, iron phosphate, cobalt phosphate, nickel phosphate, silver phosphate, zinc phosphate, cadmium phosphate, aluminum phosphate, tellurium phosphate, lead phosphate, lanthanum phosphate, magnesium sulfite, copper sulfite, cerium phosphite, barium phosphite, manganese phosphite, iron phosphite, cobalt phosphite, nickel phosphite, silver phosphite, zinc phosphite, cadmium phosphite, aluminum phosphite, tellurium phosphite, lead phosphite, lanthanum phosphite, or combinations thereof. In some examples, the water-insoluble precipitate can comprise magnesium phosphate, magnesium carbonate, zinc phosphate, copper carbonate, copper phosphate, zinc carbonate, or combinations thereof. In some examples, the water-insoluble precipitate comprises zinc carbonate.

In some examples, the water-insoluble precipitate can be dispersed substantially evenly throughout the adsorbent material. The dispersion of the water-insoluble precipitate can, for example, be quantified using STEM-EDX analysis. The elemental compositions at different regions of the adsorbent material can be measured and compared, and the error within compositions between various regions of the sample and/or the difference in elemental composition at the different regions can be used to determine the extent and/or uniformity of the dispersion of the water-insoluble precipitate in the adsorbent material.

Formation of the water-insoluble precipitate in the plurality of pores of the porous material can mean that the adsorbent material can have a BET surface area that is less than the BET surface area of the porous material. In some examples, the adsorbent material can have a BET surface area of 100 $m^2/g$ or more (e.g., 105 $m^2/g$ or more, 110 $m^2/g$ or more, 115 $m^2/g$ or more, 120 $m^2/g$ or more, 125 $m^2/g$ or more, 130 $m^2/g$ or more, 135 $m^2/g$ or more, 140 $m^2/g$ or more, 145 $m^2/g$ or more, 150 $m^2/g$ or more, 155 $m^2/g$ or more, 160 $m^2/g$ or more, 165 $m^2/g$ or more, 170 $m^2/g$ or more, 175 $m^2/g$ or more, 180 $m^2/g$ or more, 185 $m^2/g$ or more, 190 $m^2/g$ or more, 195 $m^2/g$ or more, 200 $m^2/g$ or more, 205 $m^2/g$ or more, 210 $m^2/g$ or more, 215 $m^2/g$ or more, 220 $m^2/g$ or more, 225 $m^2/g$ or more, 230 $m^2/g$ or more, 235 $m^2/g$ or more, 240 $m^2/g$ or more, 245 $m^2/g$ or more, 250 $m^2/g$ or more, 255 $m^2/g$ or more, 260 $m^2/g$ or more, 265 $m^2/g$ or more, 270 $m^2/g$ or more, 275 $m^2/g$ or more, 280 $m^2/g$ or more, 285 $m^2/g$ or more, 290 $m^2/g$ or more, 295 $m^2/g$ or more, 300 $m^2/g$ or more, 325 $m^2/g$ or more, 350 $m^2/g$ or more, 375 $m^2/g$ or more, 400 $m^2/g$ or more, 425 $m^2/g$ or more, 450 $m^2/g$ or more, 475 $m^2/g$ or more, 500 $m^2/g$ or more, 525 $m^2/g$ or more, 550 $m^2/g$ or more, 575 $m^2/g$ or more, 600 $m^2/g$ or more, 625 $m^2/g$ or more, 650 $m^2/g$ or more, or 675 $m^2/g$ or more).

In some examples, the adsorbent material can have a BET surface area of 700 $m^2/g$ or less (e.g., 675 $m^2/g$ or less, 650 $m^2/g$ or less, 625 $m^2/g$ or less, 600 $m^2/g$ or less, 575 $m^2/g$ or less, 550 $m^2/g$ or less, 525 $m^2/g$ or less, 500 $m^2/g$ or less, 475 $m^2/g$ or less, 450 $m^2/g$ or less, 425 $m^2/g$ or less, 400 $m^2/g$ or less, 375 $m^2/g$ or less, 350 $m^2/g$ or less, 325 $m^2/g$ or less, 300 $m^2/g$ or less, 295 $m^2/g$ or less, 290 $m^2/g$ or less, 285 $m^2/g$ or less, 280 $m^2/g$ or less, 275 $m^2/g$ or less, 270 $m^2/g$ or less, 265 $m^2/g$ or less, 260 $m^2/g$ or less, 255 $m^2/g$ or less, 250 $m^2/g$ or less, 245 $m^2/g$ or less, 240 $m^2/g$ or less, 235 $m^2/g$ or less, 230 $m^2/g$ or less, 225 $m^2/g$ or less, 220 $m^2/g$ or less, 215 $m^2/g$ or less, 210 $m^2/g$ or less, 205 $m^2/g$ or less, 200 $m^2/g$ or less, 195 $m^2/g$ or less, 190 $m^2/g$ or less, 185 $m^2/g$ or less, 180 $m^2/g$ or less, 175 $m^2/g$ or less, 170 $m^2/g$ or less, 165 $m^2/g$ or less, 160 $m^2/g$ or less, 155 $m^2/g$ or less, 150 $m^2/g$ or less, 145 $m^2/g$ or less, 140 $m^2/g$ or less, 135 $m^2/g$ or less, 130 $m^2/g$ or less, 125 $m^2/g$ or less, 120 $m^2/g$ or less, 115 $m^2/g$ or less, 110 $m^2/g$ or less, or 105 $m^2/g$ or less).

The BET surface area of the adsorbent material can range from any of the minimum values described above to any of the maximum values described above. For example, the adsorbent material can have a BET surface area of from 100 to 700 $m^2/g$ (e.g., from 100 $m^2/g$ to 400 $m^2/g$, from 400 $m^2/g$ to 700 $m^2/g$, from 100 $m^2/g$ to 200 $m^2/g$, from 200 $m^2/g$ to 300 $m^2/g$, from 300 $m^2/g$ to 400 $m^2/g$, from 400 $m^2/g$ to 500 $m^2/g$, from 500 $m^2/g$ to 600 $m^2/g$, from 600 $m^2/g$ to 700, or from 100 $m^2/g$ to 300 $m^2/g$).

Formation of the water-insoluble precipitate in the plurality of pores of the porous material can mean that the adsorbent material can have a pore volume that is less than the pore volume of the porous material. In some examples, the adsorbent material can have a pore volume of 0.1 $cm^3/g$ or more (e.g., 0.125 $cm^3/g$ or more, 0.15 $cm^3/g$ or more, 0.175 $cm^3/g$ or more, 0.2 $cm^3/g$ or more, 0.225 $cm^3/g$ or more, 0.25 $cm^3/g$ or more, 0.275 $cm^3/g$ or more, 0.3 $cm^3/g$ or more, 0.325 $cm^3/g$ or more, 0.35 $cm^3/g$ or more, 0.375 $cm^3/g$ or more, 0.4 $cm^3/g$ or more, 0.425 $cm^3/g$ or more, 0.45 $cm^3/g$ or more, 0.475 $cm^3/g$ or more, 0.5 $cm^3/g$ or more, 0.525 $cm^3/g$ or more, 0.55 $cm^3/g$ or more, 0.575 $cm^3/g$ or more, 0.6 $cm^3/g$ or more, 0.625 $cm^3/g$ or more, 0.65 $cm^3/g$ or more, 0.675 $cm^3/g$ or more, 0.7 $cm^3/g$ or more, 0.725 $cm^3/g$ or more, 0.75 $cm^3/g$ or more, or 0.775 $cm^3/g$ or more).

In some examples, the adsorbent material can have a pore volume of 0.8 $cm^3/g$ or less (e.g., 0.775 $cm^3/g$ or less, 0.75 $cm^3/g$ or less, 0.725 $cm^3/g$ or less, 0.7 $cm^3/g$ or less, 0.675 $cm^3/g$ or less, 0.65 $cm^3/g$ or less, 0.625 $cm^3/g$ or less, 0.6 $cm^3/g$ or less, 0.575 $cm^3/g$ or less, 0.55 $cm^3/g$ or less, 0.525 $cm^3/g$ or less, 0.5 $cm^3/g$ or less, 0.475 $cm^3/g$ or less, 0.45 $cm^3/g$ or less, 0.425 $cm^3/g$ or less, 0.4 $cm^3/g$ or less, 0.375 $cm^3/g$ or less, 0.35 $cm^3/g$ or less, 0.325 $cm^3/g$ or less, 0.3 $cm^3/g$ or less, 0.275 $cm^3/g$ or less, 0.25 $cm^3/g$ or less, 0.225 $cm^3/g$ or less, 0.2 $cm^3/g$ or less, 0.175 $cm^3/g$ or less, 0.15 $cm^3/g$ or less, or 0.125 $cm^3/g$ or less).

The pore volume of the adsorbent material can range from any of the minimum values described above to any of the maximum values described above. For example, the adsorbent material can have a pore volume of from 0.1 to 0.8 $cm^3/g$ (e.g., from 0.1 to 0.5 $cm^3/g$, from 0.5 $cm^3/g$ to 0.8 $cm^3/g$, from 0.1 $cm^3/g$ to 0.2 $cm^3/g$, from 0.2 $cm^3/g$ to 0.3 $cm^3/g$, from 0.3 $cm^3/g$ to 0.4 $cm^3/g$, from 0.4 $cm^3/g$ to 0.5 $cm^3/g$, from 0.5 $cm^3/g$ to 0.6 $cm^3/g$, from 0.6 $cm^3/g$ to 0.7 $cm^3/g$, from 0.7 $cm^3/g$ to 0.8 $cm^3/g$, or from 0.1 $cm^3/g$ to 0.4 $cm^3/g$).

In some examples, the first solution and second solution can be chosen such that the adsorbent material exhibits enhanced removal of specific gases and/or vapors (e.g., specific toxic industrial chemicals). In some examples, the first solution and second solution can be chosen such that the adsorbent material exhibits enhanced removal of acid and/or base gases.

In some examples, the adsorbent material can have an adsorption capacity for $NH_3$ gas of 0.3 mol of $NH_3$ or more per kg of adsorbent material (0.3 mol/kg or more) (e.g., 0.5 mol/kg or more, 0.75 mol/kg or more, 1 mol/kg or more, 1.25 mol/kg or more, 1.5 mol/kg or more, 1.75 mol/kg or more, 2 mol/kg or more, 2.25 mol/kg or more, 2.5 mol/kg or more, 2.75 mol/kg or more, 3 mol/kg or more, 3.25 mol/kg or more, 3.5 mol/kg or more, 3.75 mol/kg or more, 4 mol/kg or more, 4.25 mol/kg or more, 4.5 mol/kg or more, 4.75 mol/kg or more, 5 mol/kg or more, 5.25 mol/kg or more, 5.5 mol/kg or more, or 5.75 mol/kg or more). In some examples, the adsorbent material can have an adsorption capacity for $NH_3$ gas of 6 mol/kg or less (e.g., 5.75 mol/kg or less, 5.5 mol/kg or less, 5.25 mol/kg or less, 5 mol/kg or less, 4.75 mol/kg or less, 4.5 mol/kg or less, 4.25 mol/kg or less, 4 mol/kg or less, 3.75 mol/kg or less, 3.5 mol/kg or less, 3.25 mol/kg or less, 3 mol/kg or less, 2.75 mol/kg or less, 2.5 mol/kg or less, 2.25 mol/kg or less, 2 mol/kg or less, 1.75 mol/kg or less, 1.5 mol/kg or less, 1.25 mol/kg or less, 1 mol/kg or less, 0.75 mol/kg or less, or 0.5 mol/kg or less).

The adsorption capacity for $NH_3$ gas of the adsorbent material can range from any of the minimum values described above to any of the maximum values described above. For example, the adsorbent material can have an adsorption capacity for $NH_3$ gas of from 0.3 to 6 mol/kg (e.g., from 0.3 mol·kg to 3 mol/kg, from 3 mol/kg to 6 mol/kg, from 0.3 mol/kg to 2 mol/kg, from 2 mol/kg to 4 mol/kg, from 4 mol/kg to 6 mol/kg, or from 1 mol/kg to 6 mol/kg).

The adsorption capacity for $NH_3$ gas can be measured using a breakthrough apparatus where a known concentration of $NH_3$ is fed to a bed containing a known quantity of the adsorbent material and the concentration of $NH_3$ of the effluent gas coming out of the bed is monitored via mass spectrometry as a function of time. The profile of the concentration of $NH_3$ of the effluent gas coming out of the bed can then be used to calculate the $NH_3$ adsorption capacity of the adsorbent material.

In some examples, the adsorbent material can have an adsorption capacity for $SO_2$ gas of 0.05 mol of $SO_2$ or more per kg of adsorbent material (0.05 mol/kg or more) (e.g., 0.1 mol/kg or more, 0.125 mol/kg or more, 0.15 mol/kg or more, 0.175 mol/kg or more, 0.2 mol/kg or more, 0.225 mol/kg or more, 0.25 mol/kg or more, 0.275 mol/kg or more, 0.3 mol/kg or more, 0.325 mol/kg or more, 0.35 mol/kg or more, 0.375 mol/kg or more, 0.4 mol/kg or more, 0.425 mol/kg or more, 0.45 mol/kg or more, 0.475 mol/kg or more, 0.5 mol/kg or more, 0.525 mol/kg or more, 0.5 mol/kg or more, 0.575 mol/kg or more, 0.6 mol/kg or more, 0.625 mol/kg or more, 0.65 mol/kg or more, or 0.675 mol/kg or more). In some examples, the adsorbent material can have an adsorption capacity for $SO_2$ gas of 0.7 mol/kg or less (e.g., 0.675 mol/kg or less, 0.65 mol/kg or less, 0.625 mol/kg or less, 0.6 mol/kg or less, 0.575 mol/kg or less, 0.55 mol/kg or less, 0.525 mol/kg or less, 0.5 mol/kg or less, 0.475 mol/kg or less, 0.45 mol/kg or less, 0.425 mol/kg or less, 0.4 mol/kg or less, 0.375 mol/kg or less, 0.35 mol/kg or less, 0.325 mol/kg or less, 0.3 mol/kg or less, 0.275 mol/kg or less, 0.25 mol/kg or less, 0.225 mol/kg or less, 0.2 mol/kg or less, 0.175 mol/kg or less, 0.15 mol/kg or less, 0.125 mol/kg or less, or 0.1 mol/kg or less).

The adsorption capacity for $SO_2$ gas of the adsorbent material can range from any of the minimum values described above to any of the maximum values described above. For example, the adsorbent material can have an adsorption capacity for $SO_2$ gas of from 0.05 to 0.7 mol/kg (e.g., from 0.05 mol/kg to 0.4 mol/kg, from 0.4 mol/kg to 0.7 mol/kg, from 0.05 mol/kg to 0.25 mol/kg, from 0.25 mol/kg to 0.5 mol/kg, from 0.5 mol/kg to 0.7 mol/kg, or from 0.2 mol/kg to 0.7 mol/kg).

The adsorption capacity for $SO_2$ gas can be measured using a breakthrough apparatus where a known concentration of $SO_2$ is fed to a bed containing a known quantity of the adsorbent material and the concentration of $SO_2$ of the effluent gas coming out of the bed is monitored via mass spectrometry as a function of time. The profile of the concentration of $SO_2$ of the effluent gas coming out of the bed can then be used to calculate the $SO_2$ adsorption capacity of the adsorbent material.

Methods of Making

Also disclosed herein are method of making the adsorbent materials disclosed herein. In other words, also disclosed herein are methods of forming adsorbent materials. The methods of forming adsorbent materials can, for example, comprise contacting a porous material with a first aqueous solution comprising a metal cation; the porous material comprising a continuous silica phase coated with a layer comprising carbon and permeated by a plurality of pores; and contacting the porous material with a second aqueous solution comprising an anion; wherein the metal cation and the anion combine to form a water-insoluble precipitate in the plurality of pores of the porous material, thereby forming the adsorbent material. In some examples, the method can further comprise washing the adsorbent material to substantially remove a residual water-soluble ion.

The porous material can, for example, be contacted with the first aqueous solution and the second aqueous solution in any order. In some examples, the porous material can be contacted with the first aqueous solution before being contacted with the second aqueous solution. In some examples, the porous material can be contacted with the second aqueous solution before being contacted with the first aqueous solution. In some examples, the porous material can be contacted with the first aqueous solution and the second aqueous solution simultaneously.

The porous material can, for example, be contacted with the first aqueous solution for an amount of time from greater than 0 hours to 48 hours. The porous material can, for example, be contacted with the second aqueous solution for an amount of time from greater than 0 hours to 48 hours.

The metal cation can, for example, comprise a metal selected from the group consisting of Be, Mg, Al, Ca, Sc, Ti, V, Cr, Mn, Fe, Co, Ni, Cu, Zn, Ga, Sr, Y, Zr, Nb, Mo, Tc, Ru, Rh, Pd, Ag, Cd, In, Sn, Ba, Hf, Ta, W, Re, Os, Ir, Pt, Au, Hg, Tl, Pb, Bi, Ra, La, Ce, Pr, Nd, Sm, Eu, Gd, Tb, Dy, Ho, Er, Tm, Yb, Lu, Th, Pa, U, Np, Pu, Am, Cm, Bk, and combinations thereof.

The anion can, for example, comprise chloride, bromide, iodide, fluoride, sulfate, sulfide, hydroxide, phosphate, carbonate, sulfite, oxide, silicate, chromate, or a combination thereof.

In some examples, the concentration of the water-insoluble precipitate in the adsorbent material can be from 10 wt. % to 20 wt. % of the adsorbent material. The water-insoluble precipitate can, for example, have a solubility of 0.1 g or less per 100 mL of water at 20° C. Examples of water-insoluble precipitates can include nickel hydroxide, silver chloride, silver bromide, silver iodide, lead chloride, lead bromide, lead iodide, mercury chloride, copper chloride, mercury bromide, copper bromide, mercury iodide, copper iodide, thallium chloride, thallium bromide, thallium iodide, silver sulfate, lead sulfate, barium sulfate, strontium sulfate, calcium sulfate, radium sulfate, zinc sulfide, silver hydroxide, magnesium carbonate, copper carbonate, cerium carbonate, barium carbonate, manganese carbonate, iron carbonate, cobalt carbonate, nickel carbonate, silver carbonate, zinc carbonate, cadmium carbonate, aluminum carbonate, tellurium carbonate, lead carbonate, lanthanum carbonate, magnesium phosphate, copper phosphate, cerium phosphate, barium phosphate, manganese phosphate, iron phosphate, cobalt phosphate, nickel phosphate, silver phosphate, zinc phosphate, cadmium phosphate, aluminum phosphate, tellurium phosphate, lead phosphate, lanthanum phosphate, magnesium sulfite, copper sulfite, cerium phosphite, barium phosphite, manganese phosphite, iron phosphite, cobalt phosphite, nickel phosphite, silver phosphite, zinc phosphite, cadmium phosphite, aluminum phosphite, tellurium phosphite, lead phosphite, lanthanum phosphite, or combinations thereof. In some examples, the water-insoluble precipitate can comprise magnesium phosphate, magnesium carbonate, zinc phosphate, copper carbonate, copper phosphate, zinc carbonate, or combinations thereof. In some examples, the water-insoluble precipitate comprises zinc carbonate.

In some examples, the porous material can comprise a mesoporous silica coated with a layer comprising a carbonized alcohol. In some examples, the porous material can comprise MCM-41 coated with a layer comprising carbonized furfuryl alcohol. The plurality of pores can, for example, have an average characteristic dimension of from 0.1 Å to 100 Å (e.g., from 0.1 Å to 50 Å, or from 0.1 Å to 10 Å).

The porous material can, for example, have a BET surface area of from 500 to 1000 $m^2/g$. In some example, the porous material can have a pore volume of from 0.3 to 1.2 $cm^3/g$.

The adsorbent material can, for example, have a BET surface area of from 100 to 700 $m^2/g$. In some examples, the adsorbent material can have a pore volume of from 0.1 to 0.8 $cm^3/g$.

The adsorbent material can, for example, have an adsorption capacity for $NH_3$ gas of from 0.3 to 6 mol $NH_3$ as per kg of adsorbent material. In some examples, the adsorbent material can have an adsorption capacity of 2 mol of $NH_3$ or more per kg of adsorbent material.

The adsorbent material can, for example, have an adsorption capacity for $SO_2$ gas of from 0.05 to 0.7 mol of $SO_2$ or more per kg of adsorbent material. In some examples, the adsorbent material can have an adsorption capacity of 0.3 mol of $SO_2$ or more per kg of adsorbent material.

Further, the combination of the porous materials, first aqueous solution, and second aqueous solution can be conducted at various temperatures chosen to produce precipitation in the desired yield, location, and time. In general, precipitation will occur quicker at lower temperatures. So in some examples, the materials are combined at from about −4° C. to about 225° C., e.g., from about −4° C. to about 100° C., from about −4° C. to about 50° C., from about 0° C. to about 37° C., from about 0° C. to about 25° C., from about 10° C. to about 25° C., from about −4° C. to about 25° C., from about 30° C. to about 225° C., from about 50° C. to about 200° C., from about 100° C. to about 150° C., from about 100° C. to about 225° C., from about 150° C. to about 225° C., from about 30° C. to about 100° C., from about 50° C. to about 100° C., from about 30° C. to about 50° C., or from about 75° C. to about 200° C. In certain examples, the materials can be combined at room temperature.

Further, the combination of the porous materials, first aqueous solution, and second aqueous solution can be conducted at various pressures chosen to produce precipitation in the desired yield, location, and time. In general, precipitation will occur quicker at higher pressures. For example, the porous material, first aqueous solution, and second aqueous solution can be combined at any pressure (and temperature) where the first aqueous solution and the second aqueous solution are each in the liquid phase. For example, the porous material, first aqueous solution, and second aqueous solution can be combined, at room temperature, at a pressure from about 0.02 atm to about 10 atm, e.g., from about 0.02 atm to about 5 atm, from about 1 atm to about 5 atm, and from about 5 atm to about 10 atm.

In the disclosed methods, water is the primary solvent. However, in some examples cosolvents can be used. Cosolvents that can be used include one or more of the following: ketones, for example, acetone, methyl ethyl ketone, diethyl ketone, methyl n-propyl ketone, acetophenone, and cyclohexanone; linear, poly and cyclic ethers, for example, diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, 1,4-dioxane, 1,3-dioxolane, and similar compounds; and aromatic hydrocarbons, for example, toluene, ethyl benzene, xylenes, and similar compounds. Alcohols, for example, methanol, ethanol, 1-propanol, 2-propanol, isomers of butanol, isomers of pentanol, halogenated alcohols such as trifluormethanol, pentafluoroethanol, or hexafluoroisopropanol can be used as solvents alone or in combination with ketone or ether solvents. Further examples of suitable solvents include dimethylformamide, DME dimethoxyethane, dimethylacetamide, N-methylpyrrolidone, and dimethylsulfoxide. In most reactions, however, the solvent can be an ether, such as 1,4-dioxane with one or more such more alcohols, such as hexafluoroisopropanol.

If used in the disclosed methods, the amount of cosolvent can vary depending on the particular salts compound. In certain examples, from about 1 to about 200 equivalents of the solvent can be used per equivalent of the salt. For example, from about 1 to about 150 equivalents, from about 1 to about 100 equivalents, from about 1 to about 50 equivalents, from about 1 to about 10 equivalents, from about 10 to about 200 equivalents, from about 10 to about 150 equivalents, from about 10 to about 100 equivalents, from about 10 to about 50 equivalents, from about 50 to about 200 equivalents, from about 50 to about 150 equivalents, from about 50 to about 150 equivalents, from about 50 to about 100 equivalents, from about 100 to about 200 equivalents, from about 100 to about 150 equivalents, or from about 150 to about 200 equivalents, of the solvent can be used per equivalent of the salt.

Methods of Use

The adsorbent materials described herein can be used, for example, in a variety of respiration and filter applications, for example for military and/or industrial uses for the removal of toxic gases and/or vapors. In some examples, the adsorbent materials can be used in gas mask filters, respirators, collective filters, etc. The adsorbent material can also be used in other human protection devices, e.g., with a fabric. For example, a fabric comprising the adsorbent materials disclosed herein can be formed into protective clothing, e.g., coats, pants, suits, gloves, foot coverings, head coverings. Suitable fabrics that can be combined with the disclosed adsorbent materials include, but are not limited to, cotton, polyester, nylon, rayon, wool, silk, and the like.

The adsorbent materials can be used to remove gases and vapors (e.g., toxic gases) from a stream of gas or liquid. These adsorbent materials can, for example, also be used in cleaning breathing air or exhaust gases by removing various agents. The adsorbent materials can remove toxic gases etc. by chemisorption and/or physisorption of the toxic gases by the adsorbent materials. In some examples, the water-insoluble precipitate can be chosen such that the adsorbent materials is effective against a range of toxic agents in a gas stream.

Also disclosed herein are filters for removing a gas from a gas stream, said filter comprising any of the adsorbent materials described herein. Also disclosed herein are respirators comprising any of the filters disclosed herein. Also disclosed herein are gas masks comprising any of the filters described herein. The adsorbent materials, filters, respirators, and/or gas masks described herein can, for example, be used for military, homeland security, first responder, civilian, and/or industrial applications.

In some examples, the adsorbent materials, filters, respirators, and/or gas masks can be used for the removal of a gas (e.g., a toxic industrial chemical) from a gas stream. Examples of gases that can be removed include, but are not limited to ammonia, chlorine, hydrogen chloride, hydrogen cyanide, cyanogen, cyanogen chloride, sulfur dioxide, hydrogen sulfide, volatile organic compounds (VOCs) (e.g., formaldehyde, ethyl acetate, glycol ethers such as ethylene glycol, acetone, chlorofluorocarbons, chlorocarbons, benzene, methylene chloride, perchloroethylene, methyl tert-butyl ether, toluene, xylene, styrene, naphthalene, phenol, acetaldehyde, vinyl acetate, 1,4-dioxan, dimethylformamide, epichlorohydrin), and combinations thereof.

In some examples, the adsorbent materials described herein can be used as catalysts (e.g., industrial catalysts, commercial catalysts). In some examples the adsorbent materials and/or filters described herein can, for example, be used in medical applications, such as dialysis, drug intervention, etc.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Adsorbent technology can be critical in maintaining breathable air environments for diverse civilian and military applications. Filtration systems such as gas masks for military personnel and first responders are used to capture toxic industrial chemicals (TICs) from air. Described herein is the development of carbon-silica composites (CSCs) containing well-dispersed chemisorption sites of practically insoluble metal salts created via in-pore reactions. These sites can provide targeted removal capabilities for basic and acid-forming TICs such as ammonia and sulfur-dioxide.

Described herein is the synthesis of porous adsorbent materials with finely dispersed reactive sites created via in-pore synthesis. Some existing porous materials are impregnated with insoluble salts using incipient wetness and solution based approaches. The materials described herein, are made using soluble salts, which creates a precipitate of an insoluble salt within the porous materials. The in-pore synthesis of the active sites can create better dispersion of sites of interest compared to impregnation with insoluble materials. The adsorbents created via in-pore synthesis can have higher adsorption capacities compared to materials with no active sites or with poorly distributed active sites; such catalysts can be more effective on a per volume or unit mass basis. The adsorbent materials with finely dispersed reactive sites created via in-pore synthesis can be used for the capture of toxic industrial chemicals (TICs). These TICs include low concentrations of light gases such as ammonia and sulfur dioxide as representatives of basic/acid-forming gases.

The base material for the adsorbent materials is a biphasic carbon silica composite (CSC), which consists of MCM-41, a mesoporous silica, and carbonized furfuryl alcohol. Certain combinations of metal salts will react to precipitate new salts that are otherwise insoluble in water and therefore difficult to incorporate in the porous substrate (e.g., Table 1). By sequentially adding two different salts on the same substrate via incipient wetness, a reaction between the two salts is possible within the pores. Therefore, it is possible to incorporate an otherwise insoluble metal salt within a porous material by performing a precipitation reaction within the substrate using soluble reactants. These salts represent additional reactive sites to promote the adsorption of both $NH_3$ and $SO_2$ on the same material.

TABLE 1

Solubility of certain salts in water at 20° C. (g/100 mL $H_2O$).

| | $Cl^-$ | $CO_3^{-2}$ | $PO_4^{-3}$ |
|---|---|---|---|
| $K^+$ | 34 | 110 | 90 |
| $Zn^{+2}$ | 430 | $4.7 \times 10^{-5}$ | $7.7 \times 10^{-4}$ |
| $Mg^{+2}$ | 55 | $3.9 \times 10^{-2}$ | $2.6 \times 10^{-4}$ |

Figure 1:
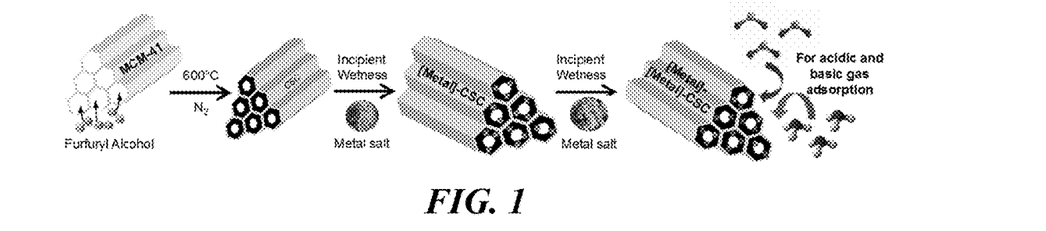
FIG. 1 displays a schematic of the synthesis of the adsorbent materials.

The CSC substrate can be functionalized with a variety of metal salts in order to introduce additional reactive sites for the increased adsorption of both $NH_3$ and $SO_2$. The synthesis of composite materials from single salt functionalizations with additional reactive sites is shown schematically in FIG. 1.

For example, insoluble zinc carbonate was precipitated in the pores of the CSC by adding zinc chloride and potassium carbonate, both of which have high water solubility. Other combinations of salts to form various insoluble precipitates (e.g., $Zn_3(PO_4)_2$, $MgCO_3$, $Mg_3(PO_4)_2$) were also tested for both $NH_3$ and $SO_2$ adsorption.

The adsorption capacities of MCM-41 and CSC containing the insoluble metal salts created via in-pore synthesis were examined. The dependence on concentration, order in which salts were added, and varying combinations of precipitates was tested against capacity performance. Each metal salt was incorporated into CSC and MCM-41 at various loadings from 10-65 wt. %.

Figure 2:
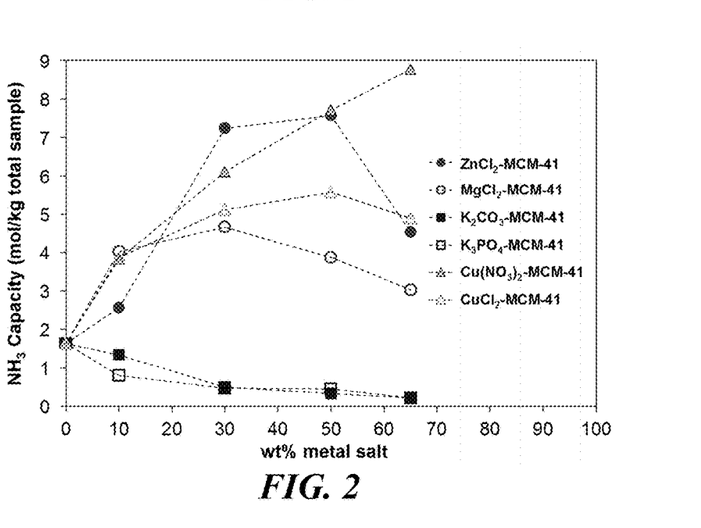
FIG. 2 displays the $NH_3$ adsorption capacities of MCM-41 with single, soluble metal salts.
Figure 3:
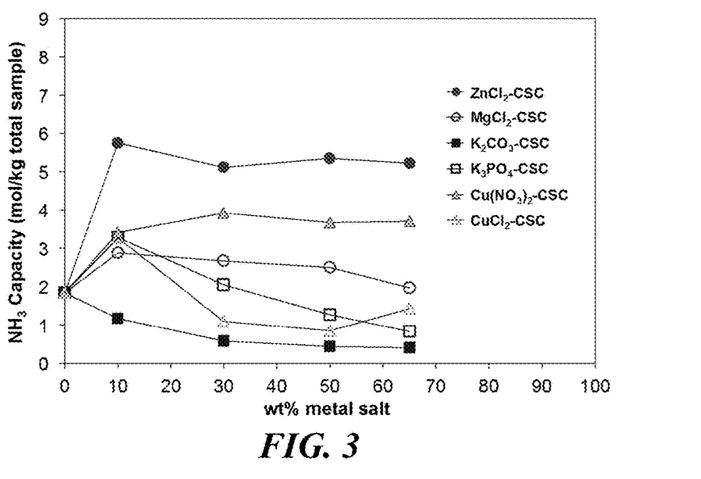
FIG. 3 displays the $NH_3$ adsorption capacities of CSC with single, soluble metal salts.
Figure 4:
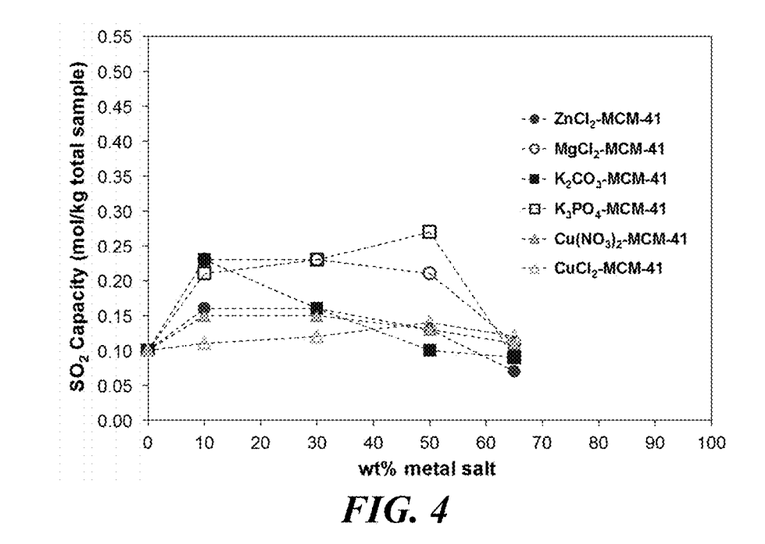
FIG. 4 displays the $SO_2$ adsorption capacities of MCM-41 with single, soluble metal salts.
Figure 5:
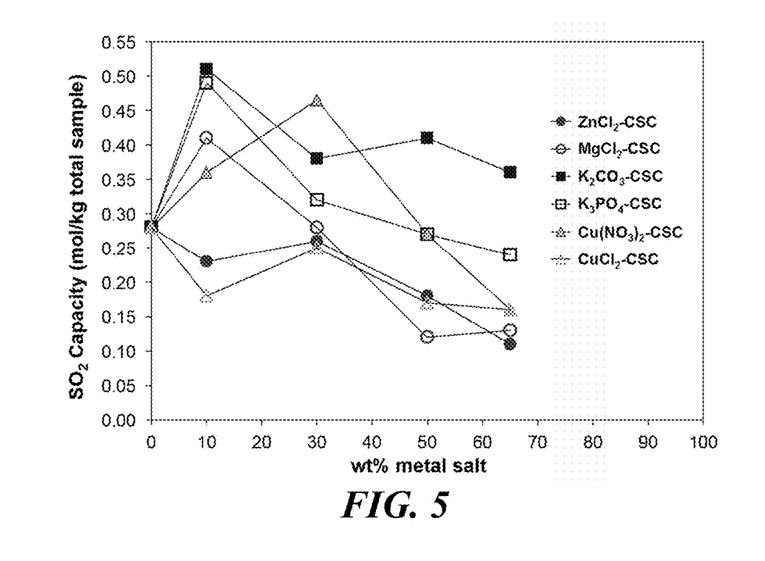
FIG. 5 displays the $SO_2$ adsorption capacities of CSC with single, soluble metal salts.

The $NH_3$ adsorption capacities of MCM-41 and CSC with single, soluble metal salts are shown in FIG. 2 and FIG. 3, respectively. The $SO_2$ adsorption capacities of MCM-41 and CSC with single, soluble metal salts are shown in FIG. 4 and FIG. 5, respectively. The $NH_3$ and $SO_2$ capacity measurements for [Metal]-CSCs shows [10 wt. % $ZnCl_2$]—CSC having the highest $NH_3$ capacity, and [10 wt. % $K_2CO_3$]—CSC having the highest $SO_2$ capacity.

The adsorption capacities of MCM-41 and CSC with insoluble metal salts are further described in Table 2. Among these dual functionalized materials, [10 wt. % $K_2CO_3$]-[10 wt. % $ZnCl_2$]—CSC, containing the insoluble precipitate $ZnCO_3$, yielded increases in adsorption capacities in comparison with non-functionalized CSC substrate and showed the highest $NH_3$ and $SO_2$ capacities ($NH_3$: 5.2 mol/kg, $SO_2$: 0.60 mol/kg).

TABLE 2

Adsorption capacities of MCM-41 and CSC with insoluble metal salts

| Insoluble Precipitate | Weight % Metal Salt in Adsorbent | | | | Adsorption Capacity (mol/kg sample) | | | |
|---|---|---|---|---|---|---|---|---|
| | $K_2CO_3$ | $K_3PO_4$ | $ZnCl_2$ | $MgCl_2$ | MCM-41 $NH_3$ | $SO_2$ | CSC $NH_3$ | $SO_2$ |
| None | 0 | 0 | 0 | 0 | 1.8 | 0.1 | 1.6 | 0.28 |
| $ZnCO_3$ | 10 | — | 10 | — | 2.3 | 0.42 | 5.2 | 0.60 |
| $MgCO_3$ | 15 | — | — | 10 | 1.6 | 0.25 | 3.5 | 0.55 |
| $Zn_3(PO_4)_2$ | — | 10 | 10 | — | 0.9 | 0.11 | 2.2 | 0.41 |
| $Mg_3(PO_4)_2$ | — | 15 | — | 10 | 0.9 | 0.10 | 2.1 | 0.53 |

Figure 6:
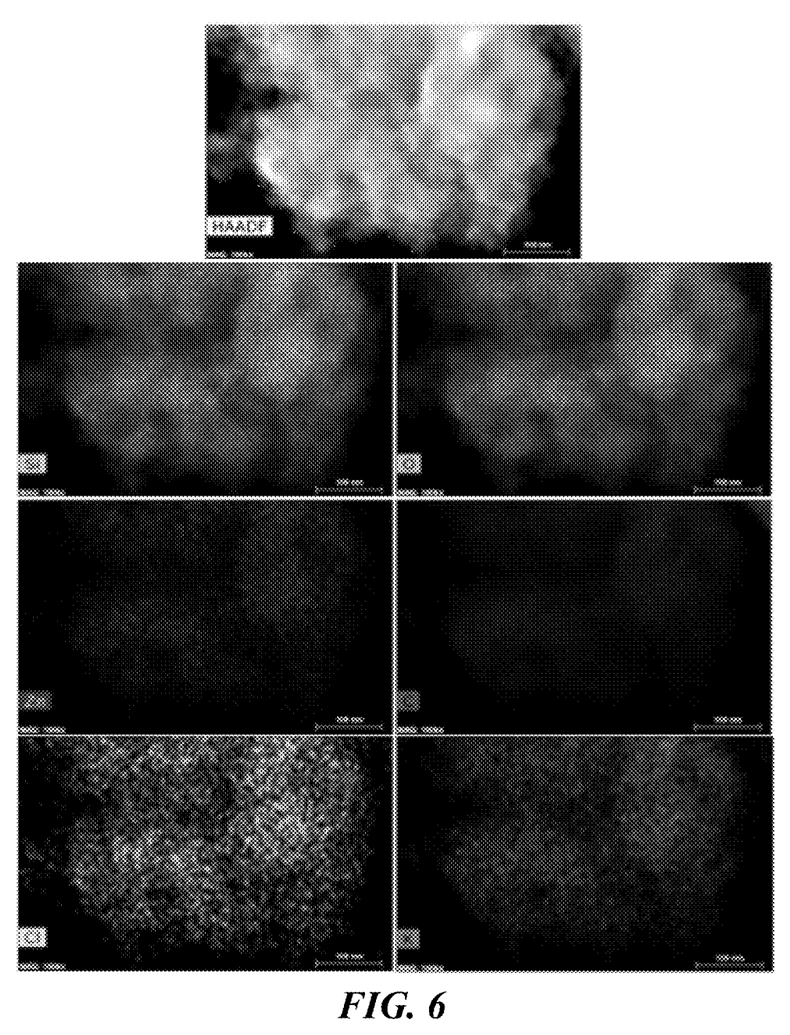
FIG. 6 shows the STEM/EDX images of the [$K_2CO_3$]—[$ZnCl_2$]-MCM-41 material.

The material composition was investigated spatially as well as quantitatively using electron microscopy. TEM images of [$K_2CO_3$]—[$ZnCl_2$]-MCM-41 show evidence of successful incorporation of both salts within the structure (FIG. 6). After in-pore synthesis, the material was washed with water to remove the residual ions of potassium and chlorine. STEM/EDX characterization provided elemental analysis of sample composition of $ZnCO_3$ synthesized in the pores of MCM-41 before and after washing.

Using TEM for quantitative analysis, the weight percent of various components in [$K_2CO_3$]—[$ZnCl_2$]-MCM-41 were assessed before and after washing with water (Table 3). Washing [$K_2CO_3$]—[$ZnCl_2$]-MCM-41 with water removed the free chlorine and potassium ions. Meanwhile, washing did not substantially affect the zinc and carbon content, suggesting that a water-insoluble $ZnCO_3$ precipitate formed within the pores of MCM-41.

The errors in composition for the $ZnCO_3$ added directly to MCM-41 by incipient wetness shows evidence of poor dispersion (Table 3). Compared with [$K_2CO_3$]—[$ZnCl_2$]-MCM-41, the incorporation of $ZnCO_3$ on MCM-41 shows a higher zinc content, however there are also large errors within the composition measurements for the incorporation of $ZnCO_3$ on MCM-41. These large errors can be the result of the poor dispersion of $ZnCO_3$ throughout the substrate. STEM/EDX shows that the zinc carbonate in MCM-41 is much more finely dispersed via the in-pore synthesis in comparison to direct addition by incipient wetness.

TABLE 3

Weight percent concentrations of components in [$K_2CO_3$]—[$ZnCl_2$]-MCM-41.

| Weight % Concentrations | Si | O | C | Zn | Cl | K |
|---|---|---|---|---|---|---|
| [$K_2CO_3$]—[$ZnCl_2$]-MCM-41 (before wash) | 44 ± 2 | 42 ± 2 | 9 ± 4 | 3.1 ± 1.5 | 1.6 ± 1.0 | 1.3 ± 0.5 |
| [$K_2CO_3$]—[$ZnCl_2$]-MCM-41 (after wash) | 48 ± 1 | 45 ± 1 | 5 ± 2 | 2.5 ± 1.0 | 0.0 ± 0.0 | 0.2 ± 0.1 |
| $ZnCO_3$-MCM-41 | 32 ± 16 | 35 ± 7 | 13 ± 7 | 20 ± 18 | 0.0 ± 0.0 | 0.0 ± 0.0 |

Adsorption capacity measurements for materials (MCM-41 and CSC) made via in-pore synthesis as well as the material made by incorporating pre-synthesized $ZnCO_3$ are shown in Table 4. The results represent an average of multiple measurements. On both the MCM-41 and CSC substrates, the incorporation of $ZnCO_3$ increased the $NH_3$ and $SO_2$ adsorption capacities, regardless of the impregnation method. Comparison between samples 2 and 6 and 1 and 5, respectively, shows that in-pore synthesis of $ZnCO_3$ improved $NH_3$ adsorption on CSC more than on MCM-41, while the improvement in $SO_2$ adsorption was more significant on MCM-41 than on CSC. In-pore synthesis of $ZNCO_3$ provided higher adsorption capacities compared with wet impregnation of the commercial $ZNCO_3$. This is due to the increased dispersion of the incorporated salt, which provides more reactive sites for adsorption compared with the incorporation of a crude, agglomerated salt containing minimal exposed reactive sites. Washed, in-pore synthesized $ZnCO_3$ on both CSC and MCM-41 was compared with crude impregnation of commercial $ZnCO_3$ on both CSC and MCM-41. Porosimetry measurements indicated that water washing increased pore volume by removing free, unreacted, soluble ions from the material. The differences in the results for the washed and unwashed samples can be attributed to the differences in the underlying substrates. On MCM-41, a comparison between samples 2 and 3 shows an increase in adsorption capacities after washing; this can be attributed to newly exposed surface hydroxyl groups that may have been previously blocked by soluble potassium and/or chloride ions. On CSC, a comparison between samples 6 and 7 shows a reduction in $NH_3$ adsorption capacity and similar $SO_2$ adsorption capacity after washing; this can be attributed to the liberation of basic carbon phase adsorption sites of the underlying CSC after the water wash, which inhibited the adsorption of basic ammonia gas.

TABLE 4

Adsorption capacities for various materials.

| Sample | Material | Adsorption Capacity (mol/kg) | |
|---|---|---|---|
| | | $NH_3$ | $SO_2$ |
| 1 | MCM-41 | 2.3 | 0.1 |
| 2 | [$K_2CO_3$]—[$ZnCl_2$]-MCM-41 (before wash) | 3.6 | 0.41 |
| 3 | [$K_2CO_3$]—[$ZnCl_2$]-MCM-41 (after wash) | 3.8 | 0.48 |
| 4 | $ZnCO_3$-MCM-41 | 3.4 | 0.44 |
| 5 | CSC | 2.1 | 0.32 |
| 6 | [$K_2CO_3$]—[$ZnCl_2$]-CSC (before wash) | 4.2 | 0.59 |
| 7 | [$K_2CO_3$]—[$ZnCl_2$]-CSC (after wash) | 2.7 | 0.56 |
| 8 | $ZnCO_3$-CSC | 3.1 | 0.44 |

Carbon silica composites are promising adsorbents for air purification applications given their potential to target a wide range of adsorbents. By incorporating small loadings of active metal sites into the porous structure of both CSCs and MCM-41, adsorption capacities show up to a threefold increase relative to impregnant-free CSC or MCM-41. Furthermore, by adding multiple salts on the same substrate not only boosts capacities for both $NH_3$ and $SO_2$ target gases, but also allows for the well-dispersed incorporation of otherwise insoluble metal salts via in-pore reaction synthesis. Microscopic evidence via TEM suggests precipitates such as $ZnCO_3$ and $Mg_3(PO_4)_2$ form on both CSCs and MCM-41. The materials made via in-pore synthesis show higher $SO_2$ adsorption capacities, both before and after washing, which can be due to the better dispersion of the adsorption sites within the material. The well-dispersed synthesis of otherwise insoluble precipitates within highly porous substrates may be suitable for a variety of catalysis or separations applications.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible examples may be made of the invention without departing from the scope thereof, it is to be understood that all matter herein set forth or shown in the accompanying drawings is to be interpreted as illustrative and not in a limiting sense.

What is claimed is:

1. A method of forming an adsorbent material, comprising:
    contacting a porous material with a first aqueous solution comprising a metal cation;
    wherein the porous material comprises a continuous silica phase coated with a layer comprising carbon and is permeated by a plurality of pores, wherein the plurality of pores have an average characteristic dimension of from 0.1 Å to 100 Å; and
    contacting the porous material with a second aqueous solution comprising an anion;
    wherein the metal cation and the anion combine to form a water-insoluble precipitate in the plurality of pores of the porous material, thereby forming the adsorbent material.

2. The method of claim 1, further comprising washing the adsorbent material to substantially remove a residual water-soluble ion.

3. The method of claim 1, wherein the porous material is contacted with the first aqueous solution before being contacted with the second aqueous solution.

4. The method of claim 1, wherein the porous material is contacted with the first aqueous solution, the second aqueous solution, or a combination thereof for an amount of time from greater than 0 to 48 hours.

5. The method of claim 1, wherein the anion comprises chloride, bromide, iodide, fluoride, sulfate, sulfide, hydroxide, phosphate, carbonate, sulfite, oxide, silicate, chromate, or a combination thereof.

6. The method of claim 1, wherein the concentration of the water-insoluble precipitate in the adsorbent material is from 10 wt. % to 20 wt. % of the adsorbent material.

7. The method of claim 1, wherein the water-insoluble precipitate comprises magnesium phosphate, magnesium carbonate, zinc phosphate, copper carbonate, copper phosphate, zinc carbonate, or combinations thereof.

8. The method of claim 1, wherein the continuous silica phase comprises a mesoporous silica and the carbon layer comprises carbonized alcohol.

9. The method of claim 1, wherein the porous material has a BET surface area of from 500 to 1000 $m^2$/g.

10. The method of claim 1, wherein the porous material has a pore volume of from 0.3 to 1.2 $cm^3$/g.

11. The method of claim 1, wherein the adsorbent material has a BET surface area of from 100 to 700 $m^2$/g.

12. The method of claim 1, wherein the adsorbent material has a pore volume of from 0.1 to 0.8 $cm^3$/g.

13. The method of claim 1, wherein the adsorbent material has an adsorption capacity for $NH_3$ gas of from 0.3 to 6 mol of $NH_3$ gas per kg of adsorbent material.

14. The method of claim 1, wherein the adsorbent material has an adsorption capacity for $SO_2$ gas of from 0.05 to 0.7 mol $SO_2$ gas per kg of adsorbent material.

15. An adsorbent material, comprising:
    a porous material comprising a continuous silica phase coated with a layer comprising carbon and permeated by a plurality of pores;
    wherein the plurality of pores have an average characteristic dimension of from 0.1 Å to 100 Å;
    wherein a water-insoluble precipitate is disposed substantially evenly throughout the adsorbent material within the plurality of pores; and
    wherein the water-insoluble precipitate comprises magnesium phosphate, magnesium carbonate, zinc phosphate, copper carbonate, copper phosphate, zinc carbonate, or combinations thereof.

16. A filter for removing a gas from a gas stream, comprising the adsorbent material of claim 15.

17. A respirator, said respirator comprising the filter of claim 16.

18. A gas mask, said gas mask comprising the filter of claim 16.

19. A human protection device, comprising a fabric and the adsorbent material of claim 15.

* * * * *